Figure 1:
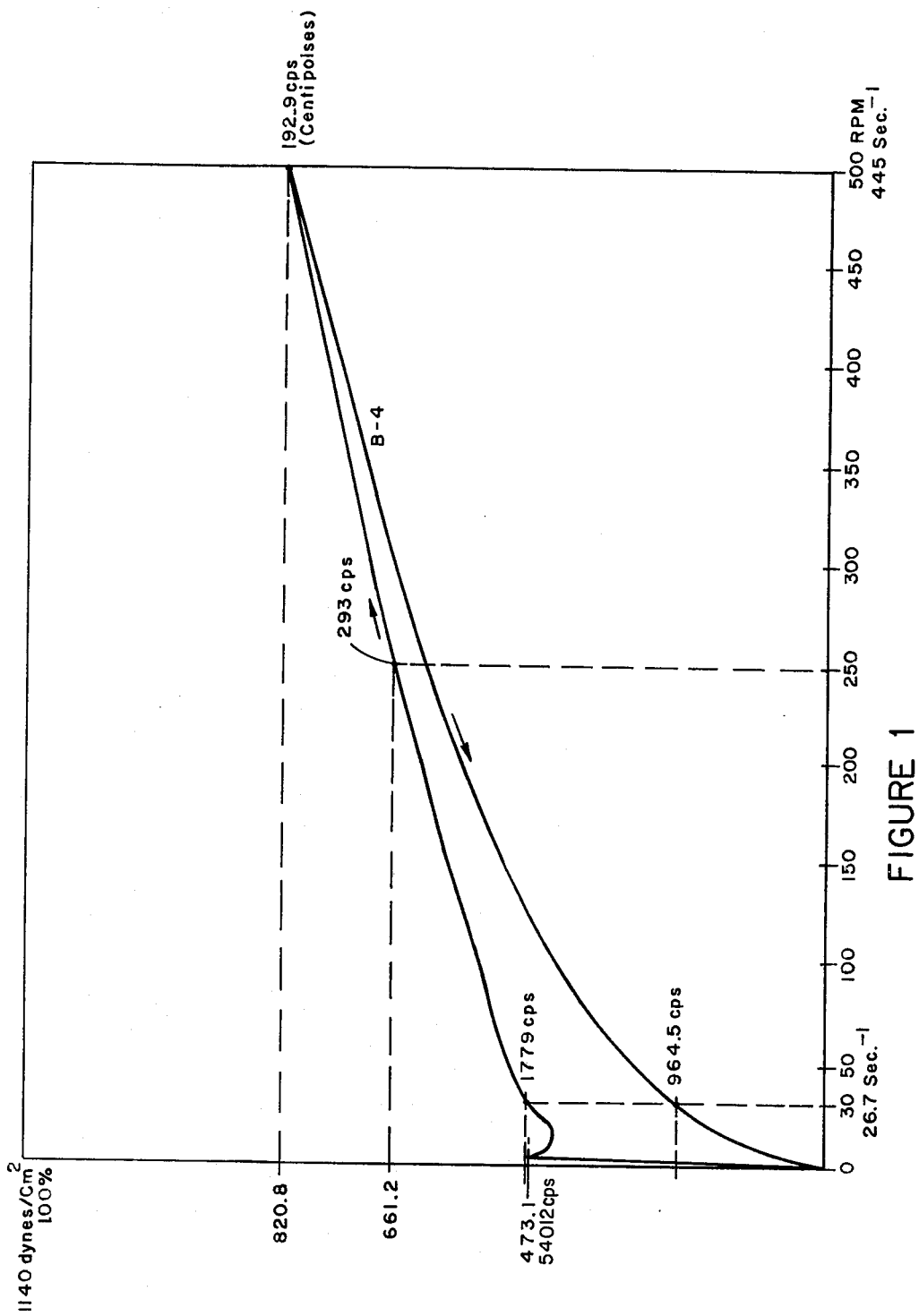

United States Patent [19]

Villamarin et al.

[11] 4,269,824

[45] May 26, 1981

[54] THIXOTROPIC HAIR CONDITIONER COMPOSITION

[75] Inventors: Arturo A. Villamarin, Mine Hill; Mabel A. S. de Gomez, Passaic, both of N.J.

[73] Assignee: American Cyanamid Company, Stamford, Conn.

[21] Appl. No.: 50,358

[22] Filed: Jun. 20, 1979

[51] Int. Cl.³ ............................................. A61K 7/06
[52] U.S. Cl. ................................. 424/70; 424/359; 424/362
[58] Field of Search ....................................... 424/70

[56] References Cited

U.S. PATENT DOCUMENTS

| | | | |
|---|---|---|---|
| 3,530,215 | 9/1970 | Greif et al. | 424/70 |
| 3,876,760 | 4/1975 | Nersesian et al. | 424/362 |
| 3,987,162 | 10/1976 | Scheuermann | 424/362 |
| 4,013,786 | 3/1977 | Cella et al. | 424/362 X |
| 4,075,131 | 2/1978 | Sterling | 424/70 X |
| 4,087,518 | 5/1978 | Smith et al. | 424/359 |
| 4,115,548 | 9/1978 | Marsh et al. | 424/70 |
| 4,144,326 | 3/1979 | Luedicke, Jr. et al. | 424/362 |

*Primary Examiner*—Dale R. Ore
*Attorney, Agent, or Firm*—Charles J. Fickey

[57] ABSTRACT

After shampoo hair conditioner compositions and, in particular, to aqueous hair conditioner compositions which exhibit unique thixotropic flow and spreading characteristics.

5 Claims, 2 Drawing Figures

THIXOTROPIC HAIR CONDITIONER COMPOSITION

The present invention relates in general to after shampoo hair conditioner compositions and, in particular, to aqueous hair conditioner compositions which exhibit unique thixotropic flow and spreading characteristics.

The hair conditioner composition of the invention comprises an aqueous composition containing a dimethyl di(hydrogenated tallow) ammonium salt, a quaternized hydrolyzed collagen protein, a cationic quaternized polymer of hydroxyethyl cellulose, and a mixture of long chain alcohols comprising at least about 90 percent by weight of $C_{16}$ and $C_{18}$ alcohols in a weight ratio of about 1 to 2, respectively.

The composition of the invention is a thick lotion having a consistency such that it may be extruded from a tube in the manner of toothpaste, which is perceived by the consumer as rich. When applied to the wet hair following shampooing, the thick lotion readily reduces in viscosity and spreads readily.

The dimethyl di(hydrogenated tallow) ammonium salt used is represented by the formula:

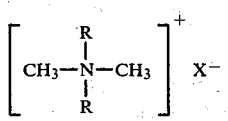

wherein X is a salt anion, preferably chloride, and R is a hydrogenated tallow fatty radical. The compound is a cationic emulsifier and provides lubricity and antistatic properties to the hair. In the present invention it is used in an amount of about 0.5 to 4.5 percent by weight, preferably about 2 to 3 percent by weight (real basis). Other cationic dimethyl di(higher alkyl)-ammonium salts may be used as a cationic emulsifier, but the aforementioned is preferred.

The hydrolyzed collagen protein derivative is a covalent quaternary ammonium compound in which 90 percent of the protein amino groups have been substituted with a quaternary of the stearyl trimethyl ammonium chloride type. The approximate molecular weight of the hydrolyzed collagen protein is 12,500. The compound is substantive to hair and provides conditioning properties, such as manageability, and shine, and also contributes to thickening and thixotropy. It is used in an amount of about 0.5 to 2.0 percent, preferably 0.75 to 1.5 percent by weight. The product is available commercially as Crotein Q (Croda, Inc.). The cationic quaternary polymer of hydroxyethyl cellulose which is preferred is Polymer JR-30M (Union Carbide Co.), which is a polymer of hydroxyethyl cellulose with N-(3-chloro-2-hydroxypropyl)trimethyl ammonium chloride having a molecular weight of about 30,000. Other similar quaternized polymers may also be used. The polymer is substantive to the hair and provides conditioning properties. It is used in the composition in an amount of about 0.1 to 0.5 percent by weight, preferably 0.2 to 0.4 percent.

The thixotropic properties of the invention are provided by a mixture of cetyl and stearyl alcohols containing at least 90 percent by weight of $C_{16}$ and $C_{18}$ alcohols in a weight ratio of about 1:2, respectively, combined with the quaternized protein, at a ratio of about 1:1 (wt) with the cetyl/stearyl alcohol mixture. The composition without the mixture of cetyl and stearyl alcohols and protein may be thick, but not thixotropic; i.e., the composition will not appear rich and thick on standing, and when applied to the hair will not exhibit the unique spreadability of the composition of the invention due to the sharp decrease of viscosity under shear. Use of either cetyl alcohol or stearyl alcohol alone results in crystallization and a decrease in viscosity on standing.*
The amount of the cetyl/stearyl alcohol mixture used in the composition will range from about 1.3 to 1.7 percent by weight of the composition.

*S. Fukushima et. al., J. Coll. and Interface Sci. 57 (2), 201–205 (1976)

A semi-solid is classified as thixotropic when its physical structure is capable of undergoing the reversible transition Gel-Sol-Gel. The transition is induced when the substance is placed under shear. The return to its original state (gel) is a time-dependent process. Under shear conditions, the viscosity of the substance drops exponentially with time of application of shear. Viscosity is the coefficient of internal "friction" which opposes flow. Its magnitude is directly proportional to the force applied to the system and to the shear stress the system offers against flow. It is inversely proportional to the rate of shear. In a plot showing shear stress vs shear rate, the coefficient of viscosity may be thought of as the slope of the resulting curve at any one point. A thixotropic substance is also characterized by requiring a minimum force to initiate flow. The force is termed "yield force" and is expressed by a "yield value" in dynes/cm$^2$.

In addition to the aforementioned components, other ingredients may be added to the composition, such as additional thickeners, e.g., hydroxyethyl cellulose; surfactants, such as polyoxyethylene ethers, e.g., the oleyl ether; freezing point depressants; solubilizers; stabilizers and preservatives; and fragrances and dyes.

The following examples illustrate the invention.

EXAMPLE 1

The following composition was prepared:

|  | Parts by Weight |
| --- | --- |
| Dimethyl di(hydrogenated tallow)ammonium chloride (75%) | 3.40 |
| Glycerine | 2.50 |
| Polyoxyethylene (2) oleyl ether | 2.00 |
| Cetyl/stearyl alcohol (93% $C_{16}$, $C_{18}$) | 1.50 |
| Quaternized hydrolyzed collagen protein | 1.00 |
| Glutaraldehyde (25%) | 0.40 |
| Hydroxyethyl cellulose | 0.40 |
| Polymer JR-30M* | 0.25 |
| Fragrance | 0.90 |
| Isopropanol, anhyd. | 0.40 |
| Dye colors | 0.001 |
| Water | qs to 100 |

*Union Carbide Co.

EXAMPLE 2

The product was prepared in the maner described in Example 1 and allowed to stand for several hours to equilibrate. A 10 ml sample was placed in a constant temperature cup (Model SVI, provided with a Rotovisco RV-3 Viscometer, Haake, Inc., Saddle Brook, N.J.). The viscometer was programmed to 25°±0.5° C. and the sensing bob was set to accelerate from 0 rpm to 100 rmp @ 50 rpm/min. and from 100 rpm to 500 rpm @ 100 rpm/min. The output from the viscometer was plotted using a Hewlett Packard X-y Recorder. In FIG. 1 the "up" curve (indicated by an arrow pointing to the right) exhibits a peak with the magnitude equal to 42% of the scale (473.1 dynes/cm$^2$). The viscosity at this point (1 rpm) is 54,012 cps. The viscosity drops (after recovery from the yield point) until at 30 rpm (shear rate=26.7 sec$^{-1}$) the viscosity is 1779 cps; at 250 rpm, the viscosity is 298 cps, and finally, at 500 rmp, the viscosity is 192.9 cps (shear rate=445 sec$^{-1}$). The "down" curve shows the viscosity profile after maximum shear has been applied. At 30 rpm, after about 10 minutes of shearing, the viscosity is 964 cps and at 1 rpm it is 9645 cps, which is a five-fold decrease from the original, indicating breakdown of the internal structure.

EXAMPLE 3

Figure 2:
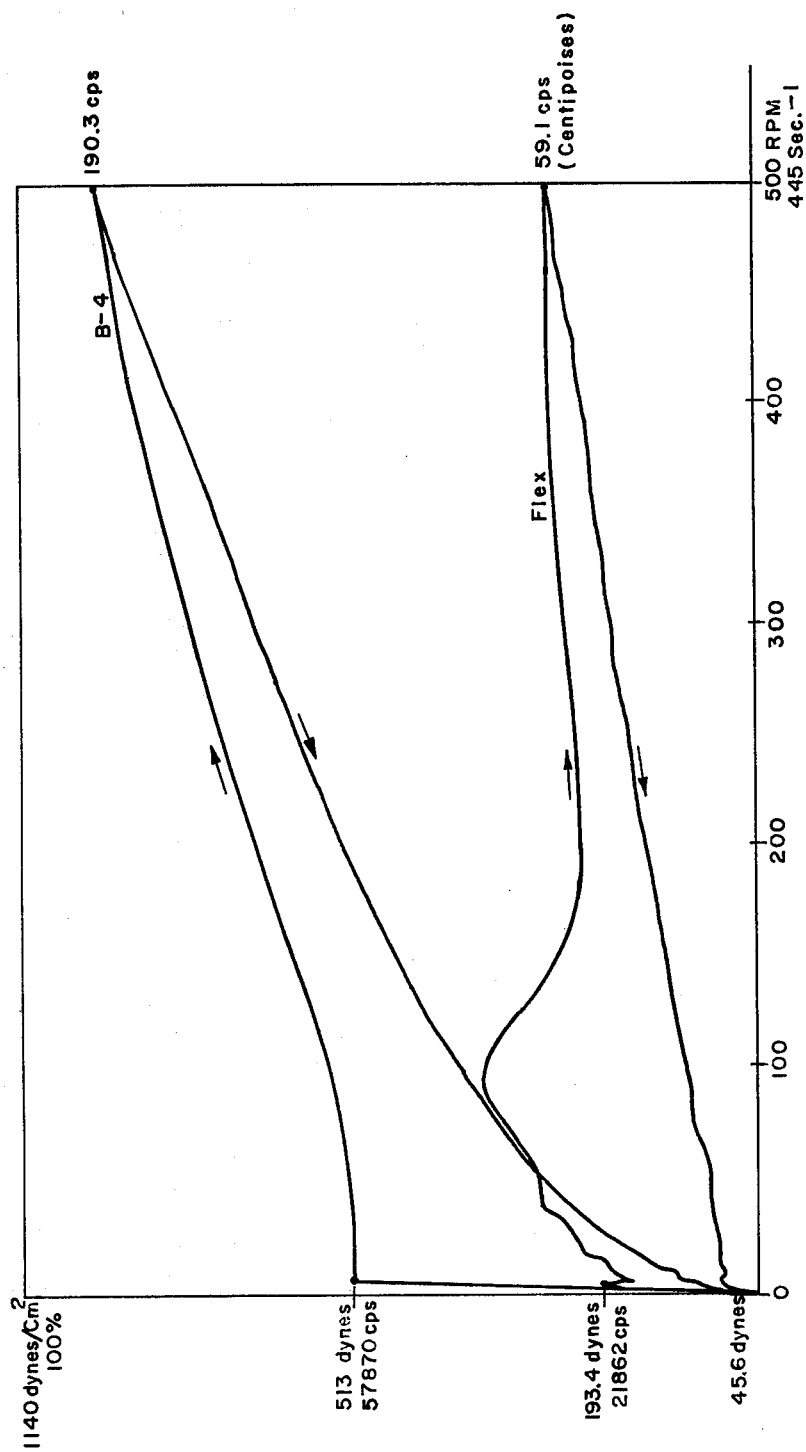

Following the procedure of Example 2, the product of Example 1 was compared with a similar competitive product (except the protein is not quaternized). FIG. 2 shows that the competitive product is dissimilar. The viscosity throughout the range measured is considerably lower, i.e., at 1 rpm, it is 21,862 cps vs 57,870; at 500 rpm, it is 59.1 cps vs 190.3 cps. The yield value is lower (193.4 dynes/cm$^2$ vs 513 dynes/cm$^2$) and the final viscosity after shear (10 minutes) is 5144 cps. The latter viscosity is similar to the viscosity of the product of the invention, which illustrates that although the viscosity is 3 times that of the competitive product on standing, it will spread with equal ease.

EXAMPLE 4

Figure 3:
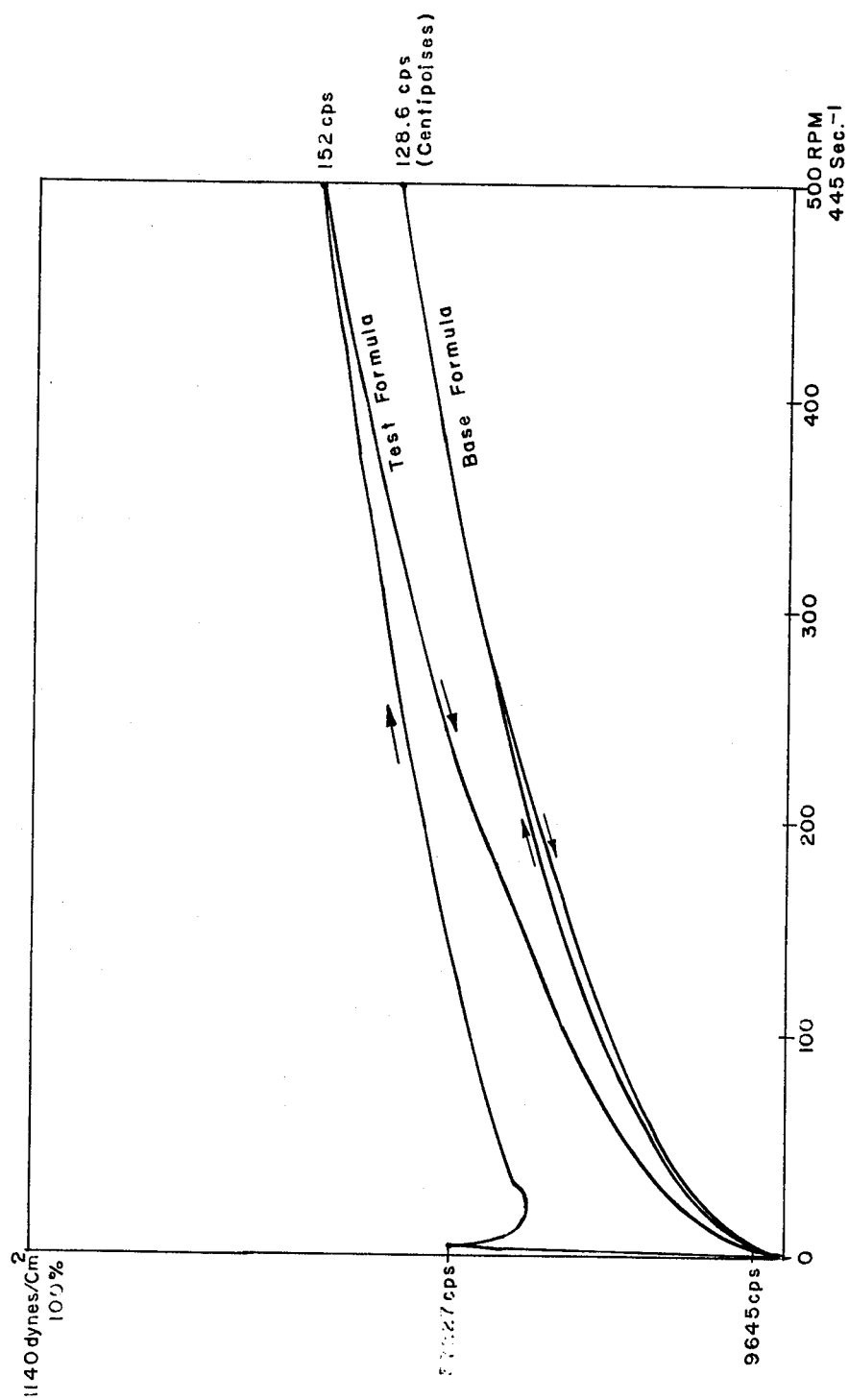

The procedure of Example 2 was followed whereby the composition of Example 1 was compared with a composition which did not contain the quaternized protein or the alcohol mixture. FIG. 3 shows that the "base formula" lacks a yield point and the curve does not form a hysteresis loop, i.e., the accelerating and decelerating plots overlap each other. No structural breakdown or thixotropy exist. After shearing for 10 minutes, the viscosity of the "base formula" retains its original value (9645 cps @ 1 rpm) while the composition of Example 1 drops from 57,227 cps to 9645 at 1 rpm.

Examples 2-4 illustrate that compositions containing unquaternized protein do not exhibit the same rheology as the composition of the invention, and that these properties are due to the mixture of cetyl/stearyl alcohol and the quaternized protein.

We claim:

1. An aqueous hair conditioner composition consisting essentially of (1) from about 0.5 to 4.5 percent by weight of a dimethyl di(hydrogenated tallow) ammonium salt, (2) from about 0.5 to 2.0 percent by weight of a quaternized hydrolyzed collagen protein in which 90 percent of the protein amino groups have been substituted with a quaternary of the stearyl trimethyl ammonium chloride type and having a molecular weight of about 12,500, (3) from about 0.1 to 0.5 percent by weight of a cationic quaternized polymer of hydroxyethyl cellulose and (4) from about 1.3 to 1.7 percent by weight, based on the weight of the composition of a mixture of long chain fatty alcohols comprising at least 90 percent by weight of said mixture of $C_{16}$ and $C_{18}$ alcohols in a ratio of about 1:2, respectively and the balance water.

2. The composition of claim 1 wherein the weight ratio of quaternized collagen protein and fatty alcohol mixture is about 1:1.

3. The composition of claim 1 wherein said ammonium salt is dimethyl di(hydrogenated tallow) ammonium chloride.

4. The composition of claim 1 wherein the amount of said ammonium salt is from about 2 to 3 percent, the amount of protein is from about 0.75 to 1.5 percent and the amount of cellulose is from about 0.2 to 0.4 percent.

5. The composition of claim 1 wherein said mixture of fatty alcohols is a mixture containing at least 90 percent cetyl alcohol and stearyl alcohol in a ratio of 1:2.

* * * * *